United States Patent [19]

Rehmer et al.

[11] Patent Number: 5,202,483

[45] Date of Patent: Apr. 13, 1993

[54] ETHYLENICALLY UNSATURATED COMPOUNDS

[75] Inventors: Gerd Rehmer, Beindersheim; Kaspar Bott, Mannheim, both of Fed. Rep. of Germany

[73] Assignee: BASF Aktiengesellschaft, Ludwigshafen, Fed. Rep. of Germany

[21] Appl. No.: 663,302

[22] Filed: Mar. 1, 1991

[30] Foreign Application Priority Data

Mar. 8, 1990 [DE]  Fed. Rep. of Germany ....... 4007318

[51] Int. Cl.$^5$ .......................................... C07C 233/09
[52] U.S. Cl. .................................... 564/207; 558/389; 560/32; 560/36; 560/42; 560/115; 560/133; 560/136; 560/140; 560/142; 562/441; 562/451
[58] Field of Search ........................ 564/207; 558/389; 560/32, 36, 42, 115, 140, 142, 133, 136; 562/441, 451

[56] References Cited

U.S. PATENT DOCUMENTS

| | | | |
|---|---|---|---|
| 3,214,492 | 10/1965 | Tocker | 260/878 |
| 3,330,656 | 7/1967 | Schuler | 564/207 X |
| 3,429,852 | 2/1969 | Skoultchi | 260/47 |
| 4,148,987 | 4/1979 | Winey | 526/316 |
| 4,281,192 | 7/1981 | Jacquet et al. | 564/207 |

FOREIGN PATENT DOCUMENTS

| | | |
|---|---|---|
| 2818763 | 11/1978 | Fed. Rep. of Germany . |
| 3820464 | 2/1990 | Fed. Rep. of Germany . |
| 3844445 | 7/1990 | Fed. Rep. of Germany . |

OTHER PUBLICATIONS

H. Kamogawa, "Facile syntheses of 2,4-dihydroxybenzophenone derivatives with polymerizable vinyl groups", J. Polym. Sci. Polym. Lett., vol 15, pp. 675–677 (1977) John Wiley & Sons, Inc.

Primary Examiner—Richard L. Raymond
Attorney, Agent, or Firm—Oblon, Spivak, McClelland, Maier & Neustadt

[57] ABSTRACT

Ethylenically unsaturated compounds of the general formula I

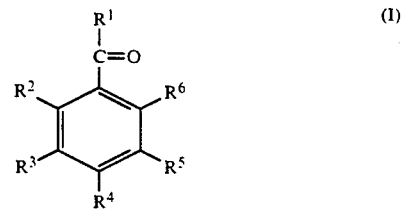

where
$R_1$ is alkyl of 1 to 4 carbon atoms, cyclopropyl, cyclopentyl, cyclohexyl, phenyl or phenyl in which some or all of the hydrogen atoms have been replaced by radicals $R^4$, not more than two substituents $R^4$ being identical, or $R^1$ together with $R^2$ or together with $R^6$ forms a $-CH_2-CH_2-$ or $-CH_2-CH_2-CH_2-$ bridge,
$R^4$ is alkyl of 1 to 24 carbon atoms, $-OH$, $-O-R^7$, $-S-R^7$,

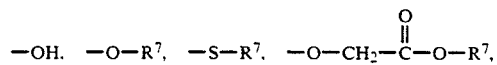

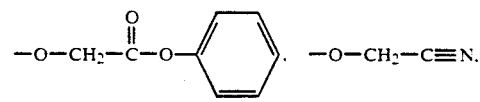

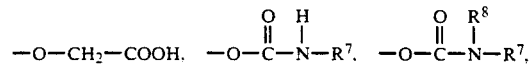

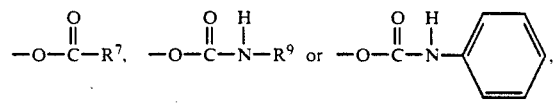

$R^2$ or $R^6$, independently of one another, both are hydrogen, or one of the radicals $R^4$, or, where $R^1$ is aryl, $R^2$ or $R^6$ is a direct bond to $R^1$ in the ortho-position with respect to the carbonyl group, and (Abstract continued on next page.)

$R^3$ and $R^5$ are each hydrogen, one of the radicals $R^4$ or a group the general formula II

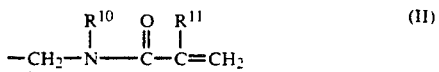 (II)

where
$R^7$ and $R^8$ are each alkyl of 1 to 4 carbon atoms,
$R^9$ is cycloalkyl of 5 or 6 carbon atoms,
$R^{10}$ is hydrogen or alkyl of 1 to 4 carbon atoms and
$R^{11}$ is hydrogen or alkyl of 1 to 4 carbon atoms,
with the proviso that either $R^3$ or $R^5$ is a group of the general formula II, are suitable for the preparation of polymers which, after exposure to actinic radiation, have increased internal strength.

4 Claims, No Drawings

ETHYLENICALLY UNSATURATED COMPOUNDS

The present invention relates to ethylenically unsaturated compounds of the general formula I

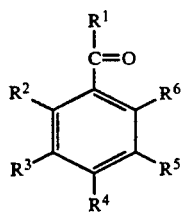

where
$R^1$ is alkyl of 1 to 4 carbon atoms, cyclopropyl, cyclopentyl, cyclohexyl, phenyl or phenyl in which some or all of the hydrogen atoms have been replaced by radicals $R^4$, not more than two substituents R. being identical, or $R^1$ together with $R^2$ or together with $R^6$ forms a —$CH_2$—$CH_2$— or —$CH_2$—$CH_2$—$CH_2$— bridge,
$R^4$ is alkyl of 1 to 24 carbon atoms, —OH, —O—$R^7$, —S—$R^7$,

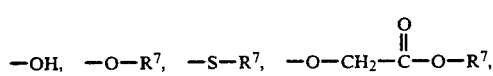

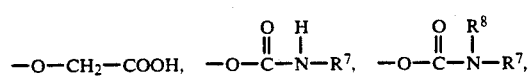

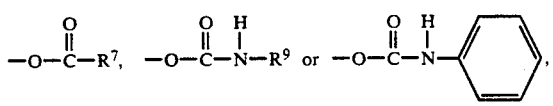

$R^2$ or $R^6$, independently of one another, both are hydrogen, or one of the radicals $R^4$, or, where $R^1$ is aryl, $R^2$ or $R^6$ is a direct bond to $R^1$ in the ortho-position with respect to the carbonyl group, and
$R^3$ and $R^5$ are each hydrogen one of the radicals $R^4$ or a group of the general formula II

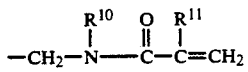

where
$R^7$ and $R^8$ are each alkyl of 1 to 4 carbon atoms, $R^9$ is cycloalkyl of 5 or 6 carbon atoms,
$R^{10}$ is hydrogen or alkyl of 1 to 4 carbon atoms and
$R^{11}$ is hydrogen or alkyl of 1 to 4 carbon atoms,
with the proviso that either $R^3$ or $R^5$ is a group of the general formula II.

The present invention furthermore relates to the preparation of compounds I and to their use as copolymerizable monomers, in particular for the preparation of polymers which have greater internal strength after exposure to actinic radiation.

Ethylenically unsaturated compounds of the general structure

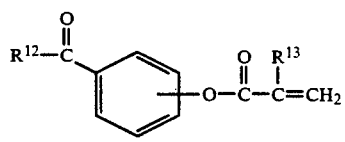

are known. They will be referred to below as ethylenically unsaturated phenones.

For example, U.S. Pat. No. 3,214,492 describes compounds of the general formula III

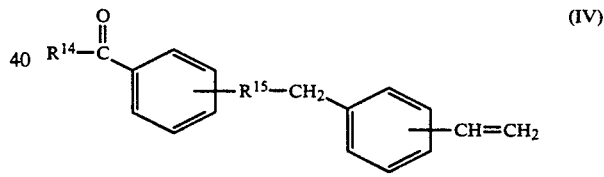

where
$R^{12}$ is —$CH_3$ or —$C_6H_5$ and $R^{13}$ is —H or —$CH_3$.

Similar acetophenone or benzophenone derivatives containing acryloxy or methacryloxy groups are disclosed in U.S. Pat. No. 3,429,852.

DE-A 28 18 763 relates to compounds of the general formula IV

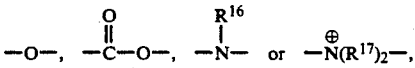

where
$R^{14}$ is —$C_nH_{2n+1}$ in which n is from 1 to 3 or —$C_6H_5$,
where
$R^{15}$ is $$-O-,\quad -\overset{O}{\underset{\|}{C}}-O-,\quad -\overset{R^{16}}{\underset{|}{N}}-\quad\text{or}\quad -\overset{\oplus}{N}(R^{17})_2-,$$

$R^{16}$ is —H or —$C_nH_{2n+1}$ in which n is from 1 to 8 and
$R^{17}$ is —$C_nH_{2n+1}$ in which n is from 1 to 4.

DE-A 38 20 464 describes, inter alia, the compounds

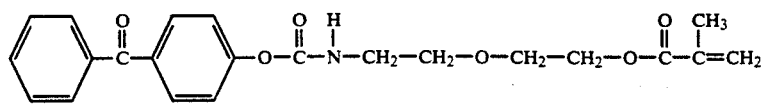

and

-continued

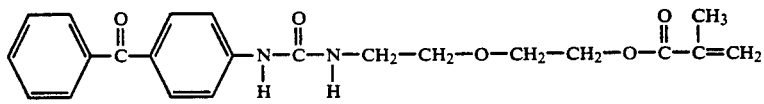

and DE-A 38 44 445 relates to ethylenically unsaturated acetophenone and benzophenone derivatives which possess a carbonate group as a coupling member between the phenone skeleton and the ethylenically unsaturated group.

The stated compounds are stated in the various publications as copolymerizable monomers for the preparation of polymers which have greater internal strength after exposure to actinic radiation. However, the disadvantage of these known ethylenically unsaturated phenones is that they do not simultaneously have the following properties:
a) high photochemical reactivity,
b) high hydrolysis stability of the link between the ethylenically unsaturated group and the phenone skeleton,
c) high thermal stability of the link between the ethylenically unsaturated group and the phenone skeleton,
d) high solubility in the comonomers,
e) simple to prepare,
f) simple to purify and
g) readily undergo free radical copolymerization.

It is an object of the present invention to provide ethylenically unsaturated phenones which are particularly suitable as copolymerizable monomers for the preparation of polymers which have high internal strength after exposure to actinic light and simultaneously have the properties a) to g) in a completely satisfactory manner.

We have found that this object is achieved by the compounds defined at the outset.

Particularly suitable compounds I are those which contain, as $R^4$, alkoxy of 1 to 4 carbon atoms, preferably methoxy or ethoxy, preferred compounds I being those in which furthermore R'' is hydrogen or methyl, $R^1$ is phenyl and $R^{10}$, $R^2$, and $R^6$ are each hydrogen.

The novel phenones are, as a rule, obtainable in a simple manner by reacting a compound of the general formula V

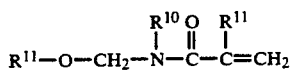 (V)

with a compound of the general formula VI

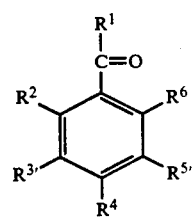 (VI)

where one of the radicals $R^3$, or $R^5$, is hydrogen and the other is a radical $R^4$.

The reaction follows the general reaction scheme VII

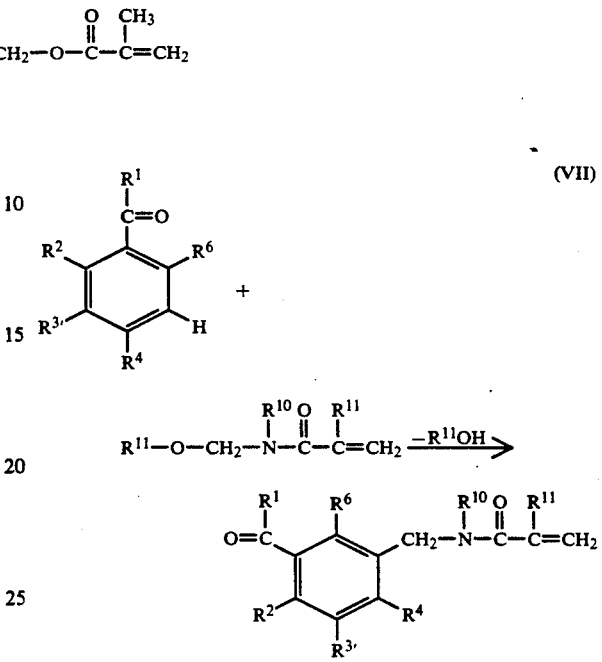 (VII)

This type of reaction is known in the literature as amidomethylation, and the associated reaction conditions are described, inter alia, in the following sources:
H. Hellmann, G. Aichinger and P. Wiedemann, J. Liebigs Ann. Chemie 626 (1959), 35
H. E. Zaug and W. B. Martin, Organic Reactions 14 (1965), 52
H. E. Zaug, Synthesis (1970), page 49.

As a rule, the compounds (V) and (VI) are used in equimolar amounts. The reaction temperature is usually from $-10°$ to $100°$ C., preferably from $0°$ to $70°$ C., particularly preferably from $5°$ to $30°$ C. The reaction is usually carried out under acid catalysis. Particularly preferred protic acids in this respect are formic acid, acetic acid, phosphoric acid, propanesulfonic acid, ethanesulfonic acid, methanesulfonic acid and particularly preferably sulfuric acid/water mixtures. The reaction can be carried out in the presence or absence of a solvent. Suitable solvents are all acid-resistant agents which are inert to amidoalkylation, are liquid under the reaction conditions and dissolve the reactants, eg. methylene chloride or acetonitrile. The reaction is preferably carried out in the absence of solvents. To suppress free radical polymerization of the unsaturated educts or products, the reaction is advantageously carried out in the presence of polymerization inhibitors.

Examples of suitable polymerization inhibitors are atmospheric oxygen, nitrobenzene, p-nitrosodimethylaniline, quinone, hydroquinone, hydroquinone monomethyl ether, 2,2-diphenyl-1-picrylhydrazyl, 2,6-di-tert-butyl-p-cresol, phenothiazine or Cu(II) salts, such as Cu(II) acetate or Cu(II) sulfate. The reaction time is as a rule from 1 to 10 hours. After the end of the reaction, the reaction mixture is subjected to hydrolysis by adding water, ice or an ice/water mixture and is worked up by a conventional method, for example by extraction with organic solvents, such as methylene chloride or diethyl ether, if necessary after temporary neutralization, and subsequent removal of the organic solvent, in order to isolate the desired product.

In advantageous cases, the desired product is precipitated in solid form directly during the hydrolysis and can be separated off by filtration. In unfavorable cases, additional measures, such as recrystallization, distillation, sublimation or zone melting, are necessary for purification, over and above the measures already stated. It may also be necessary to subject the organic solution of the reaction products to chromatographic separation. As a rule, however, the reaction takes place with good selectivity.

The starting compounds V and VI are obtainable by conventional processes or are commercially available. According to H. Feuer and U. E. Lynch, J. Am. Chem. Soc. 75 (1953), 5027 and according to U.S. Pat. No. 3,064,050, for example, N-(hydroxymethyl)methacrylamide is obtained by reacting methacrylamide with paraformaldehyde in anhydrous carbon tetrachloride.

N-(Hydroxymethyl)-acrylamide is obtainable by a similar reaction in anhydrous ethylene chloride. In both cases, the Yield usually is 70% of theory. The unsaturated carboxamide-N-methyl alkyl ethers are obtainable, for example according to E. Müller, K. Dinges and W. Graulich, Makromol. Chem. 57 (1962), 27, by the action of an alkanol on the corresponding methylol compound.

Of the compounds VI, for example, 2-hydroxy-4-methoxybenzophenone, 4,4'-dihydroxybenzophenone and 4-chloro-4'-hydroxybenzophenone are obtainable from Riedel-de Haen, D-3016 Seelze 1, and 4-aminobenzophenone, 4-methoxybenzophenone, 4-methylbenzophenone and DL-(6-methoxy-3-oxoindan-1-yl)-acetic acid are obtainable from Aldrich-Chemie, D-7924 Steinheim.

4-Hydroxybenzophenone is obtainable in a yield of about 90% of theory by Friedel-Crafts acylation of phenol with benzoyl chloride in nitrobenzene in the presence of aluminum chloride or titanium tetrachloride (Houben-Weyl 7/2a, page 186, 1973). Oxidation of 4-hydroxyphenylmethane with 5,6-dichloro-2,3-dicyano-p-benzoquinone (Houben-Weyl, 7/2a, page 681, 1973) permits the preparation of this compound in the form of a pure isomer. p-Methoxyacetophenone is obtainable by Friedel-Crafts acylation of anisole with acetyl chloride in anhydrous 1,2-dichloroethane in the presence of aluminum chloride in a yield of about 60% of theory (Organikum, 2nd amended reprint of the 15th edition, VEB Verlag der Wissenschaften, Berlin 1981).

Particularly suitable starting compounds VI are 4-methoxybenzophenone, 4-hydroxybenzophenone, 4-methylbenzophenone, p-methoxyacetophenone and p-methylpropiophenone. They are all commercially available.

In one variant for the preparation of compounds I, a simple compound VI is used as a starting material and is subjected to a reaction according to the general reaction scheme VII, and the desired product which is obtainable is derivatized by reaction of functional groups present in the desired product by conventional processes, for example by an addition reaction of isocyanates, such as phenyl isocyanate or cyclohexyl isocyanate, with —OH, or by alkylation or by alkylation. In this context, compounds VI which are of particular interest as starting compounds are those in which one or more of the substituents $R^4$, $R^6$ are hydroxyl.

As a rule, the novel phenones have completely satisfactory crystallization behavior and are usually solid at room temperature, so that they are readily obtainable in high purity by recrystallization. They are particularly suitable as copolymerizable monomers for the preparation of polymers which have high internal strength after exposure to actinic radiation. However, they can also be subjected to homopolymerization. Remarkably, they have high photochemical reactivity particularly in the short-wavelength to relatively long-wavelength UV range from 250 to 400 nm.

When the novel phenones are used for the preparation of homo- or copolymers, the usual vinyl polymerization processes can be employed in a conventional manner. For example, such polymers can be obtained by free radical mass, suspension, solution or emulsion polymerization. The polymerization of the ethylenically unsaturated phenones I can, however, also be initiated by ionic catalysts or by stereospecific catalysts of the Ziegler type.

The polymerization is preferably carried out using free radical initiators. As a rule, the products obtained have a residual content of ethylenically unsaturated phenones of less than 100 ppm when the starting amount is 10% by weight (both data relate to the total amount of starting monomer). The bond between the phenone skeleton and the polymer skeleton of the polymers obtainable in this manner has high thermal stability and high hydrolysis stability, and hence the polymers can also be processed in a satisfactory manner at elevated temperatures and the phenones I are particularly suitable for free radical aqueous emulsion polymerization processes.

Suitable comonomers of the phenones I are, for example, styrene, α-methylstyrene, acrylates and methacrylates of alkanols of 1 to 24 carbon atoms, such as methyl acrylate, methyl methacrylate, ethyl acrylate, ethyl methacrylate, n-propyl acrylate, n-propyl methacrylate, n-, tert- and isobutyl acrylate and methacrylate, 2-ethylhexyl acrylate and methacrylate, isoamyl acrylate, n-heptyl acrylate, isooctyl acrylate, isobornyl methacrylate and isobornyl acrylate, and furthermore vinyl esters of aliphatic carboxylic acids of 2 to 18 carbon atoms, e.g. vinyl acetate or vinyl propionate, and acrylamide, methacrylamide, n-vinylpyrrolidone, vinylimidazole, N-vinylformamide, N-vinylcaprolactam, acrylic acid, methacrylic acid, acrylonitrile, methacrylonitrile, maleic anhydride, itaconic anhydride, maleic acid and fumaric acid, diesters, diamides and imides of olefinically unsaturated dicarboxylic acids, e.g. maleic acid diimide, dimethyl maleate, dimethyl fumarate, di-n-butyl maleate or di-n-butyl fumarate, and the half-esters and semiamides of olefinically unsaturated dicarboxylic acids, such as mono-n-butyl maleate and mono-n-butyl-maleamide, as well as monomers, such as vinyl chloride, vinylidene chloride, vinyl fluoride, ethene, propene, butadiene, diallyl phthalate and isoprene, and mixtures of the stated monomers. Monoethylenically unsaturated compounds are preferably used as comonomers.

The novel phenones I are usually soluble in the stated monomers in a completely satisfactory manner. As a rule, the solubility under standard conditions of temperature and pressure is not less than 1 g of phenone I per 100 g of comonomers.

The amount by weight of phenones I in the copolymers is from 0.01 to 50, preferably from 0.1 to 10, % by weight, based on the copolymer, depending on requirements.

The phenones I are also particularly suitable for the preparation of graft copolymers, the phenone I being polymerized in the presence of previously prepared vinyl polymers, such as polyolefins, polyvinyl halides or polyvinyl esters.

Regardless of the polymerization process used to prepare the polymers containing the phenones I as polymerized units, the said polymers are all sensitive to actinic radiation, in particular in the wavelength range from 250 to 400 nm, and, after exposure to the said radiation, have increased internal strength. This increased internal strength is evident, for example, from increased rigidity, a higher melting point and reduced solubility of the polymer in a very wide range of solvents, and a resulting increased resistance to oils, fats, water and the like. These properties are desirable in many applications, for example when the polymers are used in photoreproduction processes. However, these properties are also advantageous when such polymers are employed for coating or impregnation. Usually, the polymer containing the phenones I as polymerized units is not exposed to actinic light until after it has been shaped into a film, a coating or another article.

The novel phenones are particularly useful for the preparation of polymers which, after exposure to ultraviolet light, are suitable as contact adhesives having high shear strength under static load. Furthermore, these contact adhesives have high peel strength. In polymerized form, they are preferably composed of a) from 0.25 to 5% by weight of one or more phenones I and b) from 95 to 99.75% by weight of one or more copolymerizable monoethylenically unsaturated monomers.

Of particular interest for contact adhesives are copolymers whose monomer composition is such that a polymer composed only of the monomers b) would have a glass transition temperature of from −45° to −0° C., particularly preferably from −30° to −10° C. According to Fox (T. G. Fox, Bull. Am. Phys. Soc. (Ser. II) 1 [1956]123), the following is a good approximation of the glass transition temperature of copolymers:

$$\frac{1}{T_g} = \frac{X^1}{T_g^1} + \frac{X^2}{T_g^2} + \ldots \frac{X^s}{T_g^s}$$

where X1, X2, ..., X5 are the mass fractions of the monomers 1, 2, ..., s and $T_g^1$, $T_{g2}$, ... $T_g^s$ are the glass transition temperatures of the particular polymers composed only of one of the monomers 1, 2, ... or s, in degrees Kelvin. The glass transition temperatures of the abovementioned monomers b) are essentially known and are stated in, for example, J. Brandrup and E. H. Immergut, Polymer Handbook 1st Ed. J. Wiley, New York 1966 and 2nd Ed. J. Wiley, New York 1975.

Furthermore, polymers suitable as such contact adhesives preferably have a K value of from 20 to 70, particularly preferably from 30 to 55, in tetrahydrofuran (THF) at 25° C., before exposure.

The K value is a relative viscosity number which is determined similarly to DIN 53,726. It incorporates the flow rate of a 1% strength by weight solution of the polymer in THF, relative to the flow rate of pure THF, and characterizes the mean molecular weight of the polymer. The initial surface tack of the contact adhesives described can be modified by adding not more than 50% by weight of tackifiers, such as coumarone-/indene, alkylphenol/formaldehyde or alkyd resins, to the novel polymers. Mineral fillers, plasticizers, polychlorinated hydrocarbons or liquid paraffins may also be added in minor amounts to the novel polymers suitable as contact adhesives, before the said polymers are used.

In terms of application technology, the novel contact adhesives are preferably used for the production of self-adhesive articles, in particular self-adhesive tapes and films, which very generally consist of a substrate and a contact adhesive. Various substrates are selected, depending on the application. Suitable ones include textile fabrics, papers, plastic films of polyvinyl chloride, polyesters, such as polyethylene glycol terephthalate, cellulose acetate or polypropylene, metal foils consisting of aluminum, copper or lead, or foams of polyurethane, polyvinyl chloride, polyethylene and polychloroprene. The novel contact adhesives are preferably applied prior to exposure to ultraviolet light. They may be applied from organic solution, preferably one having a solids content of from 50 to 80% by weight, or from the melt; where organic solutions of the novel polymers are used, the solvent is generally expelled by means of heat after coating of the substrate surface. Application is preferably effected from the melt, at from 80° to 120° C. Application may be effected in a conventional manner by spreading, spraying, roller coating, knife coating or casting. Because of the high thermal stability of the bond between the phenone skeleton and the polymer skeleton in the novel polymers, their reactivity to UV radiation is not substantially reduced even when the novel contact adhesives are processed at about 150° C.

Exposure to ultraviolet light may be effected directly after application, after removal of the solvent (application from solution) or after passage through a heating, annealing and/or cooling zone (particularly in the case of application from the melt). Exposure may be affected using commercial UV lamps, which preferably emit radiation in a wavelength range of from 250 to 400 nm. For example, medium pressure mercury lamps having a radiant power of from 80 to 120 W/cm, as described in, for example, Sources and Applications of Ultraviolet Radiation, R. Philips, Academic Press, London 1983, are suitable. The exposure time depends on the thickness of the coating, on the UV emission spectrum and on the radiant power of the radiation source used, as well as on the particular phenones I present as polymerized units. However, it can readily be determined by preliminary experiments. A protective gas need not be present during exposure.

EXAMPLES

Example 1

Preparation of various novel phenones I

For all phenones I below, the structure was confirmed by $^1$H-NMR, $^{13}$C-NMR, IR and mass spectroscopy and in some cases by independent syntheses.

a) 3-Acrylamidomethyl-4-methoxypropiophenone

A mixture of 400 g of sulfuric acid, 200 g of acetic acid, 82.0 g (0.5 mole) of 4-methoxypropiophenone, 0.2 g of di-tert-butyl-p-cresol and 55.5 g (0.55 mole) of N-methylolacrylamide was reacted for 4 hours at 20° C. and then hydrolyzed with ice. The phase obtained in solid form was separated off by filtration, taken up in 1 l of methylene chloride and purified by chromatography over a column packed with alumina.

Thereafter, the solvent was removed at 30° C. and 20 mbar and the resulting residue (92 g, crude yield=75% of theory) was stirred thoroughly with petroleum ether.

The product was obtained in analytically pure form.

Yield of pure product: 82g (66.8% of theory) mp.: 122°-124° C.

Elemental analysis:
Theory: C 67.99; H 6.93 ;N 5.66
Experiment: C 68.2 ; H 6.9; N 5.4 b) 3-Acrylamidomethyl-4-methoxybenzophenone

A mixture of 1000 g of sulfuric acid, 175.6 g (0.825 mole) of 4-methoxybenzophenone, 0.5 g of 2,5-di-tert-butyl-p-cresol and 86 g (0.851 mole) of N-methylolacrylamide was reacted for 5 hours at 25° C. and then hydrolyzed on ice.

The resulting organic phase was taken up in methylene chloride and the solution was washed several times with water. Thereafter, the solvent was removed at 30° C. and 20 mbar and the resulting residue (238 g, crude yield 98% of theory) was recrystallized from 1000 ml of a mixture of ethyl acetate and cyclohexane in a volume ratio of 5:1.

Yield of pure product: 174 g (71.6% of theory) mp.: 117°-119° C.

Elemental analysis: Theory: C 73.20; H 5.80; N 4.74; Experiment: C 73.10; H 5.7; N 4.8

The compounds c) to g) in Table 1 were obtained by similar reactions.

TABLE 1

| Starting compounds | Reaction conditions | Product |
|---|---|---|
| c) 4-Hydroxybenzophenone N-methylolacrylamide | Sulfuric acid/acetic acid | 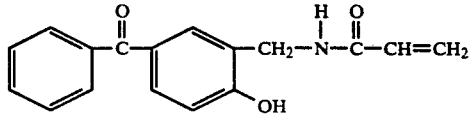<br>mp.: 160–161° C.<br>Theory: C 72.58  H 5.37  N 4.98<br>Expt.: C 72.2   H 5.5   N 4.9 |
| d) 6-Methoxy-1-tetralone N-methylolacrylamide | Sulfuric acid/acetic acid (Weight ratio 2:1) 20° C., 5 h | 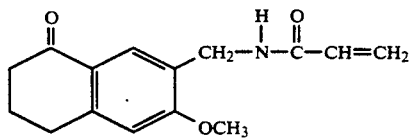 15% by wt.<br>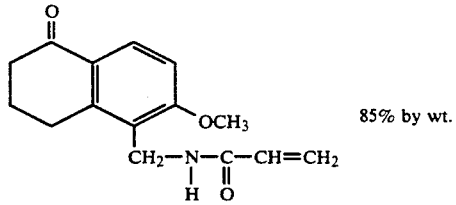 85% by wt.<br>mp. (of the mixture): 158–163° C.<br>Theory: C 69.48  H 6.61  N 5.40<br>Expt.: C 69.1   H 6.67  N 5.5 |
| c) p-Methoxyacetophenone N-methylolacrylamide | Sulfuric acid/acetic acid (Weight ratio 2:1) 15–20° C., 4 h | 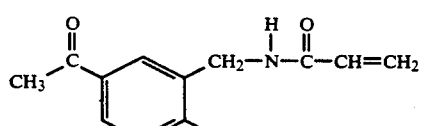<br>mp: 104–106° C.<br>Theory: C 66.94  H 6.48  N 6.00<br>Expt.: C 67.0   H 6.5   N 5.9 |
| f) p-Methylbenzophenone N-methylolacrylamide | Sulfuric acid 40–50° C., 7 h | 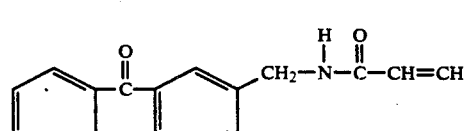<br>mp.: 149–151° C.<br>Theory: C 77.40  H 6.13  N 5.01<br>Expt.: C 77.0   H 6.3   N 4.9 |

TABLE 1-continued

| Starting compounds | Reaction conditions | Product |
|---|---|---|
| g) p-Methoxybenzophenone N-methylolmethacrylamide | Methanesulfonic acid 20–25° C., 5 h | 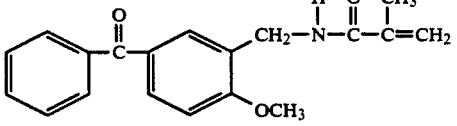 | mp. 88–90° C.
Theory: C 73.77 H 6.19 N 4.53
Expt.: C 73.7 H 6.3 N 4.5

Examples h) and i) demonstrate the possibility of subsequent functionalization of initially obtained phenones I.

h) 2-Acrylamidomethyl-4-benzoylphenoxyacetic acid

A solution of 1.97 g (0.049 mole) of sodium hydroxide in 20 ml of water was added to a mixture of 10.42 g (0.075 mole) of bromoacetic acid, 60 ml of water, 3 g (0.075 mole) of sodium hydroxide and 13.8 g (0.049 mole) of 3-acrylamidomethyl-4-hydroxybenzophenone at from 10° to 15° C., and the mixture was then kept at 80° C. for 1.5 hours.

The mixture was cooled to 20° C., after which it was acidified with 20 ml of 2N hydrochloric acid, the precipitated product was taken up in methylene chloride and the methylene chloride solution was evaporated down at room temperature. The resin-like residue (17.20 g) was dissolved in 85 ml of ethyl acetate and the solution was kept at 25° C. for 24 hours. The crystals which separated out were isolated by filtration.

Yield of pure product: 9.51 g
mp.: 154°–156° C.
Elemental analysis: Theory: C 67.25; H 5.05; N 4.13;
Experiment: C 67.1; H 5.1; N 4.0 i) 2-Acrylamidomethyl-4-benzoylphenyl N-cyclohexylcarbamate.

A mixture of 30 g (0.107 mole) of 3-acrylamidomethyl-4-hydroxybenzophenone, 13.5 g (0.108 mole) of cyclohexyl isocyanate, 0.2 g of 2,6-di-tert-butyl-p-cresol, 1.5 g of triethylamine and 180 ml of acetone was refluxed for 3 hours and then left to stand. The crystals formed were filtered off, and 26.3 g of the desired product having a melting point of 142°–144° C. were obtained in this manner. A further 13.5 g of the desired carbamate were obtained by evaporating down the mother liquor.

Example 2

Polymers which contain the novel phenones I as polymerized units and, after exposure to UV light, are suitable as contact adhesives having high shear strength
P1: 100 g of a monomer mixture 1 consisting of
840 g of isoamyl acrylate,
130 g of methyl acrylate,
30 g of acrylic acid and
0 65 g of 3-acrylamidomethyl-4-methoxybenzophenone
were heated, in 200 g of ethyl acetate (solvent) and in the presence of 4 g of 2,2'-azobis(methylisobutyrate) (polymerization initiator), to the polymerization temperature of 77° C., after which, while maintaining the polymerization temperature, the remainder of monomer mixture 1 was added in the course of 3 hours and, at the same time, a solution of 10 g of 2,2'-azobis-(methylisobutyrate) in 50 g of ethyl acetate was added in the course of 4 hours. Thereafter, polymerization was continued for 4 hours at from 75° to 85° C. and finally the solvent was distilled off.

A polymer which exhibited flow at room temperature and had a K value of 42 in THF at 25° C. was obtained.

P2: As for P 1, except that, instead of monomer mixture 1, a monomer mixture 2 consisting of
545 g of n-butyl acrylate,
300 g of 2-ethylhexyl acrylate,
130 g of N-vinylpyrrolidone,
35 g of acrylic acid and
0.55 g of 3-acrylamidomethyl-4-methoxybenzophenone was used.

A polymer which exhibited flow at room temperature and had a K value of 48 in THF at 25° C. was obtained.

Example 3

Testing of the contact adhesive properties of polymers P1 and P2 from Example 2 after exposure to UV light a) Production of the test strips

For the production of the test strips, polymers P1 and P2 were applied from their melt in a layer thickness of 25 g/m² to a polyester film as the substrate.

Thereafter, the polyester film was passed at a speed of 20 m/min and at a distance of 10 cm under two medium pressure mercury lamps (80 W/cm) arranged in series (11 cm apart). The self-adhesive film thus obtained was cut into strips 2 cm wide and 5 cm long.

b) Testing the shear strength

The test strips (a) were rolled over a length of 2.5 cm on a chromium-plated steel sheet (V2A) using a weight having a mass of 2.5 kg and were stored for 24 hours under standard conditions of temperature and humidity. The end of the steel sheet which was not involved in the adhesive bond was then fastened between two clamping jaws and the opposite projecting, freely suspended self-adhesive tape was loaded at 25° C. with a weight having a mass of 2 kg and at 50° C. with a weight having a mass of 1 kg. The time taken for breaking of the self-adhesive film is a measure of the shear strength. For comparison, the test was repeated with self-adhesive films which had not been exposed. The result is shown in Table 2.

c) Testing the peel strength

To determine the peel strength of the test strips (a) on the surface of a substrate, the said strips were rolled over a length of 2.5 cm on a chromium-plated steel sheet (V2A) using a weight having a mass of 2.5 kg. 24 hours afterward, the force required to peel off the test strips backward in a tensile test apparatus at a peel angle of 180° C. and at a speed of 300 mm/min was determined. The results are likewise shown in Table 2.

TABLE 2

| | Shear strength [h] | | Peel strength [N/cm] |
|---|---|---|---|
| | 25° C. | 50° C. | |
| P1 (exposed) | >24 | >24 | 4.3 |
| P1 | <1 | <1 | — |
| P2 (exposed) | >24 | >24 | 8.4 |
| P2 | — | <1 | — |

Example 4

Testing the thermal stability of polymer P1 and of two comparative polymers P1' and P1".

The polymers were exposed to a temperature of 150° C. for 12 hours in atmospheric oxygen. Thereafter, the polymers were investigated for crosslinked fractions and color changes. Polymers P1' and P1" differ from P1 only in that, instead of the corresponding phenone I, the following phenone monomers from DE-A 38 20 464 were used:

P1': 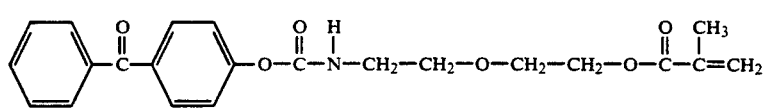

P1": 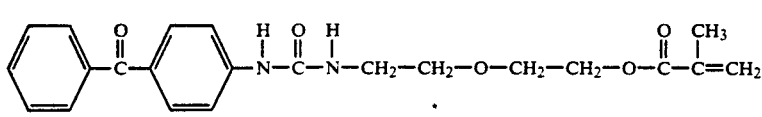

The results are shown in Table 3.

TABLE 3

| | Crosslinked fractions | Color change |
|---|---|---|
| P1 | No gel particles | None |
| P1' | Gel particles | None |
| P1" | No gel particles | Yellowish brown |

We claim:

1. An unsaturated compound of the formula I

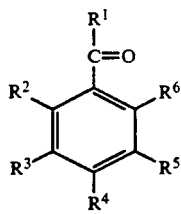   (I)

where
R$^1$ is alkyl of 1 to 4 carbon atoms, cyclopropyl, cyclopentyl, cyclohexyl, phenyl or phenyl in which some or all of the hydrogen atoms have been replaced by radicals R$^4$, not more than two substituents R$^4$ being identical, or R$^1$ together with R$^2$ or together with R$^6$ forms a —CH$_2$—CH$_2$— or —CH$_2$—CH$_2$—CH$_2$— bridge,
R$^4$ is alkyl of 1 to 24 carbon atoms, —OH, —O—R$^7$, —S—R$^7$, 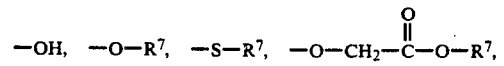

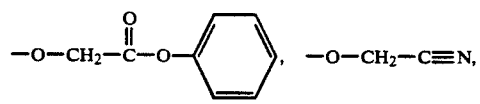, —O—CH$_2$—C≡N,

—O—CH$_2$—COOH, 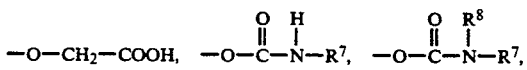

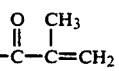, 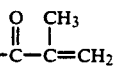 or 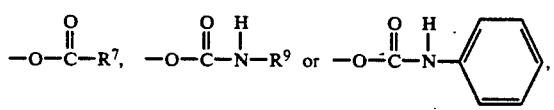,

R$^2$ or R$^6$, independently of one another, both are hydrogen, or is the said bridge with R$_1$ as above defined, or where R$^1$ is aryl, R$^2$ or R$^6$ is a direct bond to R$^1$ in the ortho-position with respect to the carbonyl group, and R$^3$ or R$^5$ are each hydrogen, one of the radicals R$^4$ or a group of the formula II

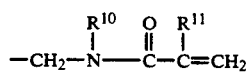   (II)

where
R$^7$ and R$^8$ are each alkyl of 1 to 4 carbon atoms,
R$^9$ is cycloalkyl of 5 or 6 carbon atoms,
R$^{10}$ is hydrogen or alkyl of 1 to 4 carbon atoms and
R$^{11}$ is hydrogen or alkyl of 1 to 4 carbon atoms, with the proviso that either R$^3$ or R$^5$ is a group of the formula II which is photoinitiatable by exposure to UV light.

2. A compound as claimed in claim 1, which contains alkoxy of 1 to 4 carbon atoms as R$^4$.

3. A compound as claimed in claim 1, which contains methoxy or ethoxy as R$^4$.

4. A compound as claimed in claim 2, which has hydrogen or methyl as R$^{11}$, phenyl as R$^1$ and hydrogen as R$^{10}$, R$^2$, R$^3$ and R$^6$.

* * * * *